United States Patent
Hansson et al.

(10) Patent No.: US 9,138,155 B2
(45) Date of Patent: Sep. 22, 2015

(54) METHOD AND A DEVICE FOR EXAMINATION OF PHYSICAL MAGNITUDE IN HUMANS OR ANIMALS IN AN OBJECT FILLED WITH LIQUID OR GAS

(75) Inventors: Tommy Hansson, Göteberg (SE); Arne Gaulitz, Billdal (SE); Hanna Hebelka Bolminger, Göteborg (SE); Svante Höjer, Kungälv (SE)

(73) Assignee: FISO Technologies Inc., Quebec (CA)

( * ) Notice: Subject to any disclaimer, the term of this patent is extended or adjusted under 35 U.S.C. 154(b) by 193 days.

(21) Appl. No.: 12/992,554

(22) PCT Filed: May 15, 2009

(86) PCT No.: PCT/SE2009/050587
§ 371 (c)(1),
(2), (4) Date: Feb. 8, 2011

(87) PCT Pub. No.: WO2009/139720
PCT Pub. Date: Nov. 19, 2009

(65) Prior Publication Data
US 2011/0124980 A1  May 26, 2011

(30) Foreign Application Priority Data
May 16, 2008  (SE) ...................................... 0801139

(51) Int. Cl.
*A61B 5/00* (2006.01)
*A61F 2/44* (2006.01)
(Continued)

(52) U.S. Cl.
CPC .............. *A61B 5/032* (2013.01); *A61B 5/0084* (2013.01); *A61B 5/4514* (2013.01); *A61B 2562/0247* (2013.01); *A61F 2/442* (2013.01); *A61F 2002/467* (2013.01)

(58) Field of Classification Search
CPC .. A61B 5/0059; A61B 5/0082; A61B 5/0084; A61B 5/03; A61B 5/032; A61B 2562/02; A61B 2562/0247; A61F 2/442; A61F 2/46; A61F 2/4657; A61F 2002/467
USPC ................................ 606/92–94, 105; 604/506
See application file for complete search history.

(56) References Cited

U.S. PATENT DOCUMENTS 5,694,946 A  12/1997  Tenerz et al.
6,277,082 B1  8/2001  Gambale
(Continued)

FOREIGN PATENT DOCUMENTS

EP  0639266  2/1995
WO  WO-98/47424 A1  10/1998
(Continued)

OTHER PUBLICATIONS

"International Application Serial No. PCT/SE2009/050587, International Search Report mailed Aug. 13, 2009", 5 pgs.

*Primary Examiner* — Christian Sevilla
*Assistant Examiner* — Eric S Gibson
(74) *Attorney, Agent, or Firm* — Fasken Martineau Du Moulin LLP

(57) ABSTRACT

The invention relates to a device for examination of a pressure (p) in an intervertebral disc, a body of vertebra or any other part of a disc in a human or animal. The device (1) comprises a hollow cannula (6) with an end portion (7) arranged to be inserted into the intervertebral disc, the body of vertebra or any other part of the disc. The device further comprises an optical fiber (8) arranged in the cannula (6) and a sensor device (10) arranged on the optical fiber (8), which in use is positioned in connection to the intervertebral disc, the body of vertebra or any other part of the disc. The device also has an injection device (11) for injection of liquid into the intervertebral disc, the body of vertebra or any other part of the disc through the cannula (6) while the sensor device (10) measures the physical magnitude (p) in the anatomical organ (2). The invention also relates to a method for examination of a pressure (p) in an intervertebral disc, a body of vertebra or any other part of a disc in humans and animals, designed in analogy to the device according to the invention.

14 Claims, 2 Drawing Sheets

(51) Int. Cl.
*A61B 5/03* (2006.01)
*A61F 2/46* (2006.01)

(56) References Cited

U.S. PATENT DOCUMENTS

| | | | |
|---|---|---|---|
| 6,370,420 | B1 | 4/2002 | Kraft |
| 2003/0181964 | A1 | 9/2003 | Sharkey et al. |
| 2004/0260240 | A1 | 12/2004 | Beyerlein |
| 2006/0011820 | A1 | 1/2006 | Chow-Shing et al. |
| 2006/0149161 | A1* | 7/2006 | Wilson et al. ............ 600/561 |
| 2007/0032747 | A1* | 2/2007 | Hashimshony et al. ...... 600/587 |
| 2007/0112299 | A1* | 5/2007 | Smit et al. ............ 604/67 |
| 2007/0287991 | A1 | 12/2007 | McKay et al. |
| 2008/0027554 | A1 | 1/2008 | Talmadge |

FOREIGN PATENT DOCUMENTS

| | | |
|---|---|---|
| WO | WO-2007/028120 A2 | 3/2007 |
| WO | WO-2007/058616 A1 | 5/2007 |
| WO | WO-2007/095752 A1 | 8/2007 |
| WO | WO 2007095752 A1 * | 8/2007 |

* cited by examiner

METHOD AND A DEVICE FOR EXAMINATION OF PHYSICAL MAGNITUDE IN HUMANS OR ANIMALS IN AN OBJECT FILLED WITH LIQUID OR GAS

RELATED APPLICATION

This application is a nationalization under 35 U.S.C. 371 of PCT/SE2009/050587, filed May 15, 2009 and published as WO 2009/139720 A1 on Nov. 19, 2009, which claimed priority under 35 U.S.C. 119 to Sweden Patent Application No. 0801139-7, filed May 16, 2008; which applications and publication are incorporated herein by reference in their entirety.

TECHNICAL FIELD

The present invention relates to a method for examination of a physical magnitude in an object filled with liquid or gas in humans and animals, comprising insertion of a tube-shaped, hollow cannula and positioning of an end portion of the cannula in said object, insertion of a sensor device with extension into the cannula, and positioning of the sensor device in connection to the object.

The present invention also relates to a device for examination of a physical magnitude in an object filled with liquid or gas in humans and animals, comprising a tube-shaped, hollow cannula arranged to be inserted into the human or animal, and comprising a first end portion leading into the object, and a sensor device arranged to be positioned in connection to the object.

BACKGROUND

In certain states of disease affecting the human backbone, for instance intervertebral disc displacement, conditions of pain provoked by the disc, so-called whiplash injuries and also other problems and injuries relating to the back such as fractures in the bodies of vertebrae, or other pathological changes in the body of vertebra or other parts of the disc, there is a need for instruments and methods of measurement for detection and analysis of the condition, in the core of each intervertebral disc respectively, which below is called disc, and in the vertebrae themselves.

Since measurement in the disc clarifies the strain on the back, there is also a need for an instrument for determination of the strain the back is subject to, e.g. during work, in specific body positions, at the carrying out of surgical operations, e.g. stabilization and/or correction operations, and for specific external strains on the vertebral column. Such a determination might be needed for medical and ergonomical reasons, but also to find a shape or design that is optimal for the strain on the back for e.g. a chair, a tool or a mattress/bed to provide a functionality and/or comfort.

Knowledge of the pressure in a disc or a body of vertebra before or after injection of fluid or pharmaceuticals can facilitate or be an indication of the reached result even in cases of e.g. so-called vertebroplastics or kyfoplastics, i.e. operations in such a form that bone cement or similar is being injected into fractured discs, preferably in elderly, to accomplish reposition, stability in the fracture and pain release.

Knowledge of the pressure conditions also in the adjacent discs or in the injured body of vertebra can increase safety in connection with these operations and also increase the possibilities to adequately fix or to reduce a fracture. The possibility, for certain pathological changes in the discs, e.g. tumours, to inject the pharmaceutical locally into the tumour also calls for knowledge of the present pressure in the changed area.

The nucleus, called nucleus pulposus, in each disc respectively, constitutes a central part of the disc and comprises a semi-liquid, gelatinous substance. The nucleus is surrounded by a peripheric portion, called anulus fibrosus, consisting of fibro cartilage. Higher up in age there is a hydrostatic pressure in nucleus pulposus. A change in pressure in the nucleus arises with altered strain on the back and with different movements. With increasing age the pressure in nucleus changes, among others due to changed properties in the nucleus and the surrounding anulus fibrosus.

A known method for investigating the nucleus in a disc is discography. Discography is thus used to evaluate if there are changes in the disc affecting the mechanical properties of the disc, but above all to establish whether the disc is a cause for back pain.

At discography a fluid is injected under pressure into the disc using for instance a syringe. The injection of fluid into a pathologically changed disc will lead to a sensation of pain for the patient. If the sensation of pain is the same or very similar to that for which the patient seeks help, the provocation of pain is interpreted as an indication that the pain, and hence the discomfort of the patient, is being generated from the examined disc. The reaction of pain is accomplished as the injected liquid generates an increased pressure in the nucleus of the disc and causes a tension or strain in an already inflamed disc tissue, or as the increased pressure causes ruptures in changed disc tissue that is a result of illness or age.

With the patent document U.S. Pat. No. 6,370,420, a system for discography is previously known wherein injection of contrast fluids and subsequent measurement is preformed of the pressure in the contrast medium that has been added to each disc, respectively, using a pressure sensor arranged outside the disc. When the pressure in the contrast medium increases in the disc, information from the measured pressure in the contrast medium, photos of the patients facial expression at the time of injection, sound recordings of the patients voice of expression, x-ray images of the disc during the injection of contrast liquid, is compiled. This compiled information then forms the basis of a subjective assessment of the patient's pain level in the disc in question and is thus no exact measuring method.

Further, through the document WO 2007/0112299 a device for injection of a liquid into a disc at discography is previously known. The device comprises pressure and volume sensors, arranged outside of the disc, for sensoring of pressure and volume in the liquid that is fed to each disc, respectively. This device measures the pressure and volume of the added liquid outside of the disc in the system, and not the actual pressure inside the disc. Even with this device a subjective assessment of the patient's pain level in the disc in question is achieved and is thus not an exact measuring method.

SUMMARY OF THE INVENTION

The object of the present invention is to accomplish a device and a method of the, by way of introduction, mentioned kind which substantially clears the problems that have been associated with devices and methods according to prior art.

This is accomplished through a method of, by way of introduction, mentioned kind comprising injection of a liquid through the cannula into the object while simultaneously measuring the physical magnitude inside the object using the sensor device.

The object is also accomplished with a device of, by way of introduction, mentioned kind, further comprising an injection device for sporadic or continuous injection of liquid into the object through the cannula while the sensor device simultaneously measuring the physical magnitude in the object.

The object of the present invention is to eliminate the lacks in prior art. Specifically the invention relates to measuring, with high precision, the actual pressure inside an object such as for instance an anatomical organ, independent of factors such as injection rate and injected liquid volume.

A further object of the invention is to achieve, with its increased sensitivity, a more objective assessment of the condition on each disc, respectively, i.e. without having to confide in the subjective sensation of pain in an anatomical organ for the patient.

A preferred embodiment of the invention relates to a method for examination of a physical magnitude in an object in the form of an anatomical organ in humans and animals. The method comprises preferably insertion of a tube-shaped, hollow cannula and positioning of the cannulas first end portion in the anatomical organ and insertion of an optic fibre which extends into the cannula, and positioning of a sensor device, arranged on the optic fibre, in connection to the organ. The method according to the embodiment further comprises injection of liquid through the cannula into the anatomical organ while at the same time measuring the physical magnitude inside the anatomical organ using the sensor device.

The method according to the invention preferably comprises a comparison of the measured value for the measured anatomical magnitude with a predetermined threshold value, and injection of a liquid which appropriately constitutes a contrast liquid.

The method according to the invention appropriately comprises x-ray examination of the anatomical organ and a measurement of the pressure, which measurement appropriately is based on optical interference.

The term "object filled with liquid or gas" in this connection relates to an element that can absorb liquid or gas, and functioning as a "void" wherein the present pressure can be measured. As examples of such objects filled with liquid or gas, anatomical organs, e.g. heart, liver, discs, vertebrae and bodies of vertebrae, or other objects inside a human or animal body, e.g. a tumour, can be mentioned.

A method according to the invention preferably relates to examination of a physical magnitude in an anatomical organ in humans and animals, which organ may be an intervertebral disc, a disc or a body of vertebra. The device comprises a tube-shaped, hollow cannula arranged to be inserted in the human or the animal. The cannula has a first end portion leading into the anatomical organ and an optic fibre arranged with its longitudinal extension in the cannula, a sensor device arranged on the optical fibre, which in use is positioned in connection to the anatomical organ. The device further comprises an injection device for continuous injection of liquid, such as for instance a contrast medium, bone cement or a pharmaceutical, into the anatomical organ through the cannula while the sensor device measures the physical magnitude in the anatomical organ. The sensor device is arranged on a first end portion of the optical fibre. The sensor device further comprises a pressure sensor, which sensor suitably is an optical sensor. The optical sensor is for instance a Fabry-Perot sensor.

A circumstance that is present in using discography is that the hospital personnel making the diagnosis must rely on the patient telling them when experiencing pain. The pressure being measured during injection is the pressure that is accomplished in the liquid from the syringe and is thus measured outside of the disc. The measurement of pressure and injection of liquid is thus not preformed independent of each other. The pressure accomplished in the disc is thus not measured. Instead the patient's subjective sensation of e.g. pain must be taken into account when diagnosing, which makes it difficult to obtain exact measurement results.

With discography there is also a risk that the disc is damaged when more and more liquid is injected under increasing pressure, without control of the pressure inside the disc. There is also a risk that falsely positive results are obtained if the pressure in the disc during injection of liquid becomes so high that the tissues in the discs are damaged. If a sufficiently high pressure is not accomplished during injection of fluid for other reasons, e.g. solderations in the disc, there is a risk of falsely negative results.

In a fractured disc, knowledge of the pressure during injection of bone cement or other substance, can clarify if the injected substance stays in the body of vertebra, as intended, or tends to leak outside of the same. Registration of pressure can in this case constitute a security measure to avoid damages on surrounding tissues.

DESCRIPTION OF THE DRAWINGS

The invention will now be described based on the enclosed drawings. These illustrate.

DESCRIPTION OF THE EMBODIMENTS

Figure 1:
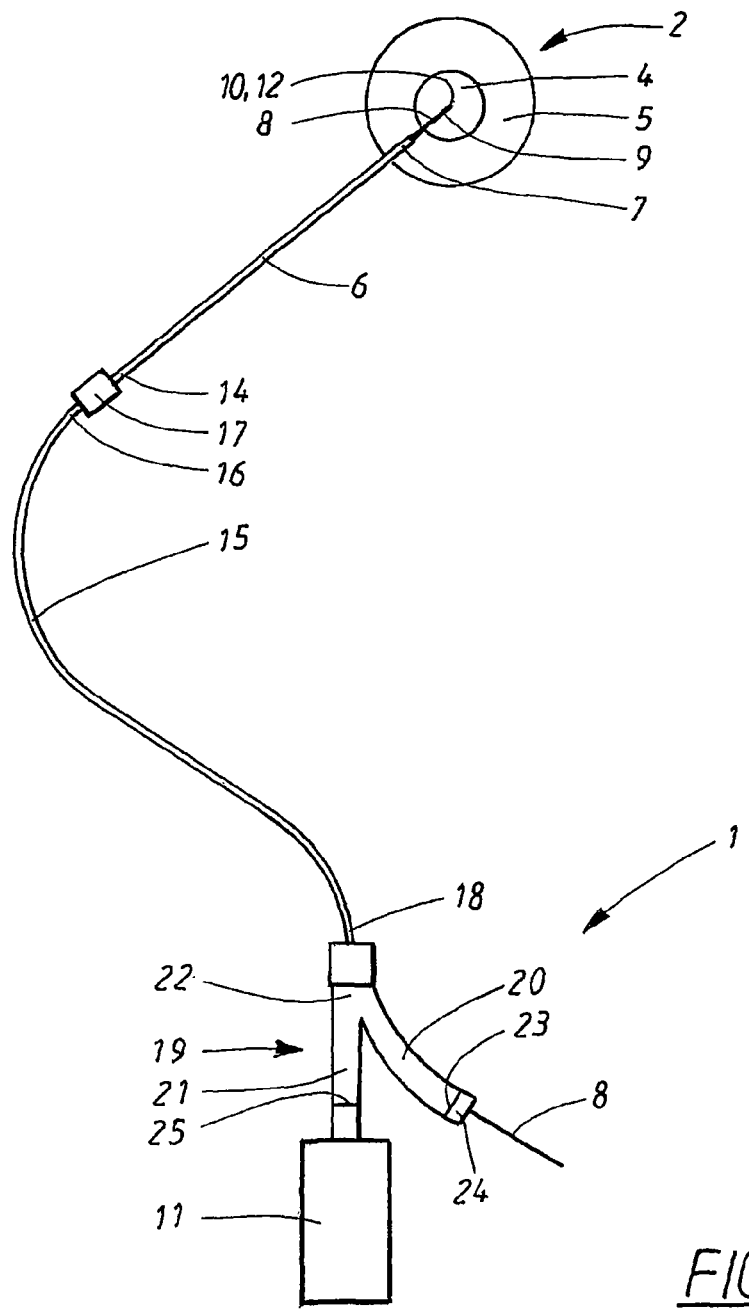
FIG. 1 a schematic view of a device according to the invention.

FIG. 1 illustrates schematically a device 1 for examination of a physical magnitude, e.g. pressure (p), in an anatomical organ 2. In the description below the invention will be described with reference to a preferred example of embodiment intended for examination in a human body 3. However, the invention can also be used in connection with a corresponding type of examination in an animal body. In general the invention can be used for examinations in different objects filled with liquid or gas, e.g. heart, liver, discs, vertebrae and bodies of vertebrae, but also objects such as tumours.

The invention is illustrated in the drawings during use in connection with a examination procedure for measuring a physical magnitude (p), such as for instance pressure, temperature etc. in an anatomical organ 2, such as e.g. nucleus pulposus 4, which constitutes the nucleus in a vertebra disc in the human body. This examination procedure is used in certain states of disease or changes in the disc or its proximity such as e.g. in so called discogenic pain where it may be desired to measure the pressure inside the nucleus pulposus 4. Nucleus pulposus 4 comprises a semi-liquid, gelatinous substance and is surrounded by a ring shaped portion of fibro cartilage, called anulus fibrosus 5.

The device 1 comprises a tube-shaped, hollow cannula 6, arranged to be inserted in the human or animal. The cannula 6 is extended and has a first end portion 7, or a point, arranged in the anatomical organ 2. The cannula 6 is preferably manufactured in metal. Alternatively, the cannula 6 can be manufactured by another material that is "MR-compatible", i.e. that is suitable in light of the use in connection with magnetic resonance spectroscopy equipment. This use is characterised by very powerful electromagnetic fields which in their turn places demands on what kind of materials that may be used. In the scope of the present invention the cannula 6 can therefore be manufactured by a hard plastic material.

In the cannula 6 there is an optical fibre 8 arranged with its longitudinal extension in the cannula 6. The cannula 6 has an inner measurement which is larger than the outer measurement of the optical fibre 8. In the cannula 6 the optical fibre 8 is movable back and forth wherein a first end portion 9 on the optical fibre 8 can assume a predetermined position in relation to the first end portion 7, or point, of the cannula 6. For instance the optical fibre 8 is arranged so that its first end portion 9 extends a small portion out of the first end portion 7 of the cannula 6. The optical fibre 8 can also assume a protected position through its first end portion 9 being positioned inside the first end portion 7 of the cannula 6. Suitably the optical fibre 8 has a diameter in the range of 0.08-0.5 mm, but the invention is not limited to such a dimension, but the diameter can have another dimension.

On the optical fibre 8 there is a sensor device 10 arranged, which, when in use, is positioned in connection to the anatomical organ 2. The sensor device 10 is arranged on the first end portion 9 of the optical fibre 8.

In cases where the sensor device 10 is arranged in a protected position inside the first end portion 7 of the cannula 6, this can be used, for instance, to perform pressure measurements on two differently defined positions for the sensor device 10, one in connection to the first end portion 7 of the cannula 6, and one inside the first end portion 7 of the cannula 6, and then generating a combined value in respect of the pressure, based on both of these pressure measurements using a display and measurement unit 13. If one of the positions comprises a protected position inside the first end portion 7 of the cannula 6, it is ensured that the measurement from this position only will reflect the hydrostatical pressure in the nucleus pulposus, and no influence by possible mechanical pressure that may affect the sensor device 10. Alternatively to using a protected position, an alternative may be to use another position that may be outside of the first end portion 7 of the cannula 6.

With the intention to protect the optical fibre 8 and the sensor device 10, the entire cannula 6 can be fitted into a protective device in the shape of a tube-like casing. This version is particularly suitable when the invention is being used to inject a liquid in the form of bone cement in an anatomical organ. This casing may then suitably have an outer diameter in the range of approximately 0.5-1.5 mm.

The device 1 further comprises an injection device 11 for continuous injection of liquid into the anatomical organ 2 through the cannula 6, while the sensor device 10 measures the pressure (p) in nucleus pulposus 4. The injection device 11 can e.g. constitute a syringe through which the liquid is injected into the device 1. The injected liquid is preferably a contrast medium, wherein the propagation in or leakage of the liquid from the anatomical organ 2 can be determined using x-ray. In cases where a magnetic resonance spectroscopy is being used, the entire device 1 is manufactured of a plastic material.

The sensor device 10 registers the pressure in the injected liquid in the nucleus pulposus 4, wherein the actual pressure in the nucleus pulposus 4 can be measured. The sensor device 10 further comprises a sensor body for measurement of pressure (p), which is an optical sensor 12. Preferably an optical pressure sensor of the type Fabry-Pérot is being used. This type of pressure sensor is previously known and illustrated in for instance the patent document EP 0639266. The sensor device 10 further comprises the display and measurement unit 13, with which the measured pressure is displayed.

The cannula 6 has a second end portion 14, connected to a first end portion 16, of a soft, bendable tube 15, through a connection device 17. The purpose of the connection device 17 is to connect the cannula 6 with the tube 15. The tube 15 is preferably manufactured by plastics. Another end 18 of the tube 15 is connected to an attachment device 19, which in the illustrated embodiment is substantially V-shaped and hollow wherein the attachment device 19 has a first branch 20 and a second branch 21. An attachment portion 22 of the attachment device 19 is connected to the tube 15 and is in common for both the first and the second branch 20, 21. The first branch 20 has an insertion opening 23 wherein the optical fibre 8 is inserted. In order to seal the device 1 from contaminants and prevent injected liquid from pressing out, the insertion opening 23 is equipped with a sealing 24, through which the optical fibre 8 runs. The optical fibre 8 thus runs through the attachment device 19, the tube 15, the connection device 17 and the cannula 6. The second branch 21 on the attachment device 19 is equipped with an injection opening 25 to which the injection device 11 is arranged.

The purpose of the tube 15 is to provide a distance to the human body 3, to minimize the bearing pressure against the body, when injecting the liquid into the device 1. Further the tube 15 and the attachment device 19 have inner measurements that are wider than the external measurements of the optical fibre 8.

Figure 2:
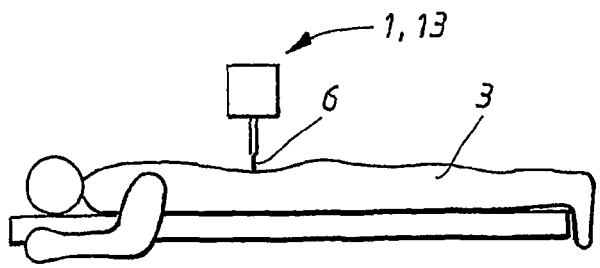
FIG. 2 a schematic view of the device according to the invention, during use in examination of a human.

FIG. 2 represents a schematic view of the invention 1 wherein an examined human 3 is lying on a couch, back facing up.

Below the method for examination of an anatomical organ 2 according to the invention will be described and will be described based on a measurement of pressure. When measuring the pressure in an anatomical organ 2, e.g. nucleus pulposus 4, a tube-shaped, hollow cannula 6 is inserted through the back in a position close to the nucleus pulposus on the human 3 or animal wherein the measurement is to be conducted. In order to facilitate the insertion of the cannula 6, it is possible to first make an opening in the skin of the human or animal. An optical fibre 8 is inserted in the cannula 6, and the optical fibre 8 has its extension in the cannula 6. The cannula 6 may be connected to the connection device 17, the tube 15 and the attachment device 19, before or optionally after the optical fibre 8 has been inserted into the cannula 6.

The sensor device 10, which is arranged on the optical fibre 8, is positioned in connection to the anatomical organ 2. Thereafter, sporadic or continuous injection of liquid is preformed through the cannula 6 into the anatomical organ 2, while measuring the physical magnitude, in this case the pressure p, inside the anatomical organ using the sensor device 10.

The value of pressure p being measured by the sensor device 10 is compared to a predetermined threshold value. The comparison of the measured value and the predetermined value is accomplished in a display and measurement unit 13. Suitably this threshold value is set at a level corresponding to a previously defined condition in the present organ 2. E.g. the threshold can correspond to a condition in the organ 2 which in turn can be used as some form of medical assessment of the patient wherein the measurement has been preformed. In this way a substantial disadvantage in prior art is set aside, more exactly the medical assessment is to large extent based on information from the patient about the experienced pain due to the injection of liquid. In stead, according to the invention, a more objective measuring method is accomplished.

The system can be adjusted to measurements at different pressure levels so that an adaption can be made for the object in which a measurement is to take place. For instance, pressure levels in the range of 50-360 mbar can be present at a measurement in objects such as heart, liver and tumours. Alternatively, pressure levels in the range of 0-20 bar can be present at measurement in objects such as discs, vertebrae and bodies of vertebrae. Suitably the system can be equipped with different sensor devices depending on what pressure level is concerned in each measurement application.

Figure 3:
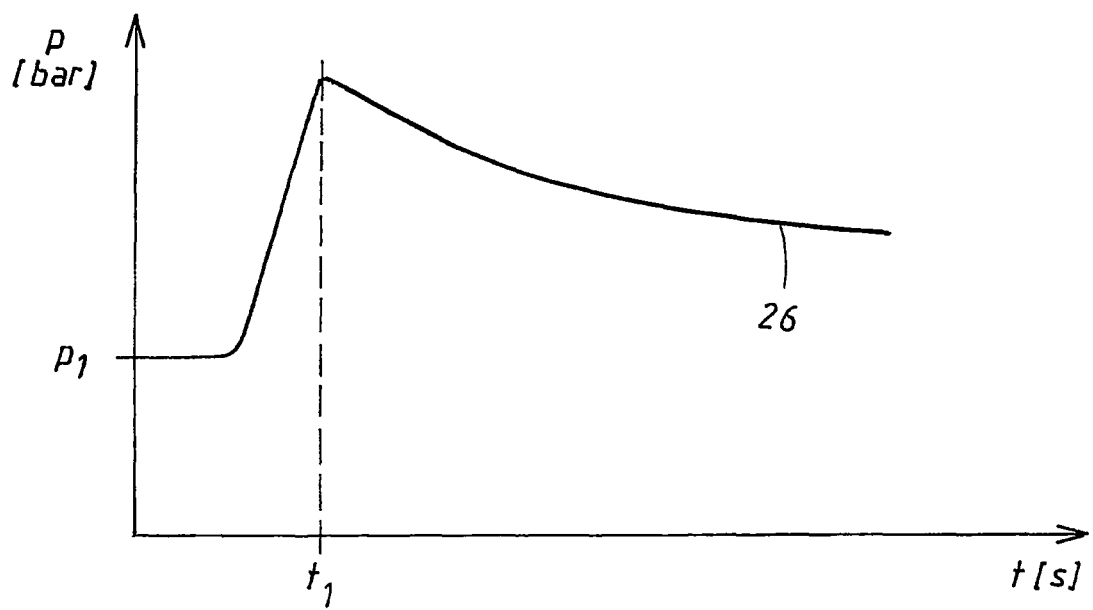
FIG. 3 shows a diagram with which the function of the invention is explained.

FIG. 3 is a diagram showing how the pressure (y-axis) depends on time (x-axis) when injecting liquid using the invention. The example in the drawing corresponds to injection during pressure of a fluid in a disc. The diagram shows a graph 26 that can be presumed to correspond to a healthy disc. The method is initiated by measuring the pressure p, which then is at a given level p1, without any other specific measures being taken. Thereafter liquid is being fed under a certain pressure and at a certain flow rate, causing the pressure inside the disc to gradually increase. At a certain time t1 the feeding of liquid is stopped, not the least to prevent the disc from being injured by too high a pressure. Thereafter the pressure level is allowed to decrease gradually during a certain amount of time.

The progress being illustrated with the graph 26 follows a certain progress which to a relatively high degree is predictable. If there should be a significant deviation from this predicted progress, i.e. a deviation from the expected presentation of the graph, this deviation can be interpreted as there being a defect present in the disc wherein the pressure is being measured.

The injected liquid can be a contrast medium or any other substance, for instance bone cement or a pharmaceutical. Following injection of contrast medium or bone cement, an x-ray examination can be preformed of the anatomical organ to ascertain the propagation of the liquid in, or possibly leakage from, the anatomical organ 2. The measurement of the pressure p is based on optical interference.

The invention is not limited to that which is stated above, but to all embodiments that are possible within the scope of the claims.

For example the invention can be used to measure the pressure in a number of discs simultaneously. This then implies that one sensor device per disc is connected to the measurement and guiding device for simultaneous and substantially continuous measurement of the pressure p in each disc, respectively. By monitoring the pressure changes in the different discs, information can be gathered of possible discs where great deviations from the expected result have been obtained. In that way, possibly defect discs can be identified. When measuring multiple discs, the corresponding graphs (cf. FIG. 3) can be drawn. Possible deviations in one or more graphs compared to an expected presentation can then indicate that there is a defect present.

Further, the invention can be used to measure another physical magnitude than pressure, e.g. the temperature.

The invention claimed is:

1. A diagnostic method for assessing the medical condition of an object filled with liquid or gas in humans and animals based on a physical parameter (p) measured in the object, the method comprising:
    inserting a tube-shaped, hollow cannula, and positioning an end portion of the cannula, inside the object;
    introducing a sensor device into the cannula;
    positioning the sensor device relative to the object;
    injecting a liquid through the cannula into the object for a predetermined time period while measuring the physical parameter (p) inside the object using the sensor device; the physical parameter (p) being chosen from the group consisting of: (a) pressure; and (b) temperature;
    comparing a profile of measured values of the physical parameter (p) to a profile of predetermined values of the physical parameter (p); the profile of measured values of the physical parameter (p) representing a plot of the measured values of the physical parameter (p) against time values of the predetermined time period; the profile of predetermined values representing a plot of the predetermined values of the physical parameter (p) against the time values of the predetermined time period; each predetermined value of the physical parameter (p) and associated time value corresponding to a previously defined medical condition of the object;
    determining the medical condition of the object based on the comparison of the profile of measured values to the profile of the predetermined values.

2. The method of claim 1 wherein the step of injecting includes continuously injecting the liquid through the cannula into the object while continuously measuring the physical parameter (p) inside the object using the sensor device.

3. The method of claim 1 wherein the object is selected from the group consisting of: (a) an anatomical organ; (b) an intervertebral disc; (c) a vertebra; and (d) a tumour.

4. The method of claim 1 wherein the liquid is selected from the group consisting of: (a) a contrast medium; (b) a bone cement; and (c) a pharmaceutical.

5. The method of claim 1 further comprising, following the step of injecting the liquid, determining one of propagation of the liquid in the object and leakage of the liquid from the object, using x-rays.

6. The method of claim 1 further comprising the step of locating the sensor device within the object using x-rays.

7. The method of claim 1 wherein the profile of the predetermined values represents a profile of values for a healthy object.

8. The method of claim 1 wherein the sensor device includes an optical sensor.

9. The method of claim 8 wherein the optical sensor is a Fabry-Pérot optical sensor.

10. The method of claim 8 wherein:
    the physical parameter (p) is pressure; and
    the step of measuring the physical parameter (p) inside the object using the sensor device includes measuring the pressure inside the object based on optical interference.

11. The method of claim 1 wherein the step of positioning the sensor device relative to the object includes arranging the sensor device so as to be wholly contained within the cannula.

12. The method of claim 1 wherein the step of positioning the sensor device relative to the object includes arranging the sensor device outside the cannula.

13. The method of claim 1 wherein:
    the physical parameter (p) is pressure; and
    the step of measuring the physical parameter (p) inside the object using the sensor device includes measuring the pressure inside the object based on optical interference.

14. The method of claim 1 wherein:
    the object is an intervertebral disc having a nucleus pulposus;
    the step of inserting includes inserting the tube-shaped, hollow cannula, and positioning an end portion of the cannula, inside the nucleus pulposus;
    the physical parameter (p) is pressure; and
    the step of measuring the physical parameter (p) inside the object includes measuring the pressure inside the nucleus pulposus using the sensor device.

* * * * *